US00PP21912P3

(12) United States Plant Patent
Fotinos

(10) Patent No.: US PP21,912 P3
(45) Date of Patent: May 10, 2011

(54) *HYDRANGEA* PLANT NAMED 'HYDTHREE'

(50) Latin Name: *Hydrangea macrophylla*
Varietal Denomination: HYDthree

(76) Inventor: Peter Fotinos, Santa Barbara, CA (US)

( * ) Notice: Subject to any disclaimer, the term of this patent is extended or adjusted under 35 U.S.C. 154(b) by 0 days.

(21) Appl. No.: 12/315,940

(22) Filed: Dec. 9, 2008

(65) Prior Publication Data

US 2010/0146675 P1 Jun. 10, 2010

(51) Int. Cl.
*A01H 5/00* (2006.01)

(52) U.S. Cl. ..... Plt./250

(58) Field of Classification Search ..... Plt./250
See application file for complete search history.

*Primary Examiner* — Susan B McCormick Ewoldt

(57) ABSTRACT

A new *Hydrangea* plant, which has abundant, pink or blue colored double flowers and attractive foliage. The variety successfully propagates from softwood cuttings and is suitable for year round production in commercial glass houses as a flowering pot plant. This new and distinct variety has shown to be uniform and stable in the resulting generations from asexual propagation.

4 Drawing Sheets

Latin name of genus and species: *Hydrangea macrophylla* 'HYDthree'.

Variety denomination: The new variety is named 'HYDthree'.

BACKGROUND OF THE INVENTION

The present invention constitutes a new and distinct variety of *Hydrangea* plant, which was developed by artificially pollinating an unnamed seedling(not patent in the US) with an unnamed seedling (not patent in the US). The two parents were crossed in the spring of 2005 and the resulting seed was sown in September 2005, in a controlled glasshouse environment. Out of these seedlings one seedling was selected, as the new variety and named 'HYDthree'. The new *Hydrangea* plant may be distinguished from its seed parent, an unnamed seedling, by the following combination of characteristics:

1. The unnamed seedling has a breeding background in unnamed seedlings.
2. 'HYDthree' has medium dome-shaped inflorescences, while the unnamed seedling has large dome-shaped inflorescences.
3. 'HYDthree' has pink or blue colored flowers, while the unnamed seedling has white flowers.

The new variety may distinguished from its pollen parent, an unnamed seedling created by the same inventor, by the following combination of characteristics:

1. The unnamed seedling has a breeding background in unnamed seedlings.
2. 'HYDthree' has medium dome-shaped inflorescences, while the unnamed seedling has small flat inflorescences. 'HYDthree' has pink or blue flowers, while the unnamed seedling has red flowers.

BRIEF SUMMARY OF THE INVENTION

Initial asexual reproduction of 'HYDthree' by cuttings was first done in Santa Barbara, Calif., USA. The reproduction was conducted in controlled greenhouse environments.

Have here proven that the foregoing and all after characteristics and distinctions to come true to form and are established in succeeding propagations. 'HYDthree' is a low and compact *Hydrangea* plant with good vigor.

The objective of the hybridization of this *Hydrangea* variety for commercial greenhouse culture was to create a new and distinct variety with:

1. Uniform and abundant flowers with good keepability;
2. Attractive long lasting foliage and compact growth,
3. Year round flowering under glasshouse conditions;
4. Suitability for production from softwood cuttings in pots.;
5. Durable flowers and foliage which make the variety suitable for distribution in the floral industry.

This combination of qualities was not present in previously available commercial cultivars of this type and distinguish 'HYDthree' from all other varieties of which we are aware.

The seeds, from hybridization were planted in a controlled environment and evaluations were conducted on the resulting plants. 'HYDthree' was selected by Peter Fotinos, in his development program in Santa Barbara, Calif., USA.

BRIEF DESCRIPTIONS OF THE DRAWINGS

The accompanying color illustrations show as true as is reasonably to obtain in color photographs of this type, the typical characteristics of the buds, flowers, leaves, stems of 'HYDthree'. Specifically illustrated in the drawings:

On sheet sheet ¼:
FIG. 1: Development of Pink flowers.
FIG. 2: Developments of blue flowers.
FIG. 3: Tip of young shoot.
FIG. 4: Mature leaf, upper side.
FIG. 5: Mature leaf, reverse side..

On sheet ²⁄₄:
FIG. 6: Bare stem with flower head starting to unfold.
FIG. 7: Corymb with flowers detached.

On sheet ³⁄₄:
FIG. 8: Corymb fully unfolded blue.

On sheet ⁴⁄₄:
FIG. 9:Corymb fully unfolded pink.

DETAILED BOTANICAL DESCRIPTION OF THE VARIETY

The following is a detailed description of the *Hydrangea* plant: *Hydrangea macrophylla* 'HYDthree'.

The following observations, measurements, values and comparisons describe plants grown in glass houses in Santa Barbara, Calif., USA.

The age of the observed plants where 29 to 33 weeks after propagation by cuttings, and produced as flowering pot plants in container of 16 centimeter in diameter.

Environmental conditions in the cultivation area for the observed plants, has been temperatures from 36 to 78 degree Farenheit, and 10 to 20 hours day length with assimilation light. Light levels from 600 foot candle to 6000 foot candle. The relative humidity has been ranging from 50 to 85%.

Color references are made using The Royal Horticultural Society (London, England) Colour Chart, 1995, except where common terms of color are used. For a comparison, the nearest existing *Hydrangea* variety is 'RIE 12', a *Hydrangea* variety described and illustrated in U.S. Plant Pat. No. PP 17,833. Chart 1 details several physical characteristics of 'HYDthree' and 'RIE 12'.

CHART 1

| Chart 1: | 'HYDthree' | 'RIE 12' |
|---|---|---|
| Sepal color, Upper surface | Red Group 49A to 49D or Blue Group 106B to 106D | Purple Group 75B |
| Sepal color, Reverse surface | Red Group 49A to 49D Or Blue Group 106B to 106D | Purple Group 75C |
| Petal count | 25 to 30 | 16 average |

*Parents.*—Unnamed seedling×unnamed seedling.

Classification:

*Botanical.*—*Hydrangea macrophylla.*

*Commercial.*—Pot *Hydrangea.*

Plant:

*Plant growth.*—Moderately vigorous. Grows compact upright to bushy. When grown as 11 cm pot plant, the average height of the plant itself is 20 to 22 cm, and average width is 21 cm. When grown as a 16 cm pot plant, the average height of the plant itself is 24 to 36 cm, and average width is 30 cm. The plantform is rounded.

Production time is generally 29 to 33 weeks depending on average temperature, light level, and cultural practices.To create pink flower heads the plants was grown at pH 6.0. To create blue flower heads the plants was grown at pH 4.5 and Aluminum at 20 ppm was added to the irrigation water.

Stem:

*Color.*—Young wood: Green Group 143 D, with intonations of Greyed-Purple Group 187C, at the internode base Older wood: Green Group 141C, with intonations of Greyed-Purple Group 187C, at the internode base.

*Lenticels.*—Incidence: 120 to 140 per internode. Size: 0.3 to 0.5 mm Color: Greyed-Purple Group 187C. Shape: Round to ovate.

*Surface.*—Young wood: Smooth Older wood: Smooth.

*Stem diameter.*—4 to 5 mm.

*Internode length.*—20 to 40 mm.

*Numbers of internodes.*—5 to 6.

Plant foliage: Leaves arranged alternately, generally symmetrical, abundant, and flat in aspect. The venation pattern is pinnate.

*Quantity of leaves.*—10 to 12 per lateral branch(branch).

*Petioles.*—Color: Green Group 143D, Margins: Entire Length: 12 to 18 mm Diameter: about 3 to 4 mm.

*Leaves.*—Edge: Serrated. Serration: Single. Shape: Ovate with acuminate apex and obtuse to acuminate base. Texture: Coriaceous Appearance: Dull Size: Length: 60 to 90 mm. Width: 35 to 60 mm Color: Young foliage: Upper surface: Green Group 137B Lower surface: Green Group 143C Color: Mature foliage: Upper surface: Yellow-Green Group 137B Lower surface: Green Group 143C Leaf vein color: Upper surface: Yellow-Green Group 144D. Reverse surface: Yellow-Green Group 144D.

Inflorescense:

*Blooming habit.*—Seasonal, natural flowering in spring-summer season.

*Fragrange.*—None.

*Flower type.*—Single flowers densely arranged on a corymb spherical formed head. Corymb size: 15 to 20 cm in diameter. Fertile Flowers: none. Sterile flowers: 125 to 140 per flower head, with 20 to 25 sepals per flower.

*Flowerbuds.*—Length: 1 to 2 mm. Diameter: 1 to 2 mm. Shape: Ovoid. Color: Yellow-Green Group 145B.

*Peduncle.*—Color: Yellow-Green Group 143D, with intonations of Grey-Purple Group 187D. Texture: Smooth, with lenticels of Grey-Purple Group 187D Length: 25 to 35 mm Diameter: 2 to 3 mm. Strength: Erect, strong. Count: 3 to 4 per stem.

*Pedicel.*—Color: Greyed-White Group 157D, with intonations of Grey-Purple Group 187C to 187D, and for aluminum treatment also intonations of Violet-Blue Group 90D towards the end of the pedicel. Texture: Smooth Length: 15 to 25 mm Diameter: 1 to 2 mm. Count: 8 to 10 per peduncle. Strength: Erect, strong

*Sterile flower.*—Form: Shape of flower when viewed from the side. Up on opening: Cupped Open flower: Flat Size: 35 to 65 mm in diameter Sepals: 20 to 25 per sterile flower, Sepal size: Length: 5 to 15 mm. Width: 3 to 15 mm Sepal shape: Orbicular with emarginated tip. Texture: Smooth. Margin: Single serrated. Appearance: Dull. Color: At emerging flower head Upper surface: At pH 6.0: White Group 155D, with intonations of Yellow-Green Group 144A. At pH 4.5: White Group 155D, with intonations of Yellow-Green Group 144A. Reverse surface: At pH 6.0: White Group 155D, with intonations of Yellow-GreenGroup 144A. At pH 4.5: White Group 155D, with intonations of Yellow-Green Group 144A. Full unfolded flower head Upper surface: At pH 6.0: Red Group i the range from 49A to 49D, Intonations of Yellow Group 10C as center of each Sterile flower. At pH 4.5: Blue Group in the range from 106B to106D. Intonations of Yellow Group 10C as the center of the sterile flowers Reverse surface: At pH 6.0: Red Group in the range from 49A to 49D, Intensity is increasing towards the veins. At pH 4.5: Blue Group in the range from106B to106D. Intensity is increasing towards the veins. Eye: Color: Yellow Group 10C Size: 0.5 to 2 mm in diameter.

Development:

*Vegetation.*—Dense.

*Blooming.*—Abundant.

*Aptitude to bear fruit.*—Poor.

*Resistance to diseases.*—Above average resistance to mildew and Botrytis under normal growing conditions in Santa Barbara, Calif. Seeds has not been observed due to that the plant has never been grown to the stage of seed development, due to the fact, that the variety is developed for use as a flowering pot plant only.

*Winter hardiness & Drought/heat tolerance.*—Due to the fact, that this variety is a potted flowering plant, developed indoor use only, the plant are not tested for winter hardiness or drought/heat tolerance.

I claim:

1. A new and distinct variety of *Hydrangea* plant, substantially as herein illustrated and described as a distinct and novel *Hydrangea* variety due to its abundant pink or blue double flowers, attractive long lasting foliage, vigorous and compact growth, year round flowering under glasshouse conditions, suitability for production from softwood cuttings in pots, and durable flowers and foliage which make the variety suitable for distribution in the floral industry.

* * * * *

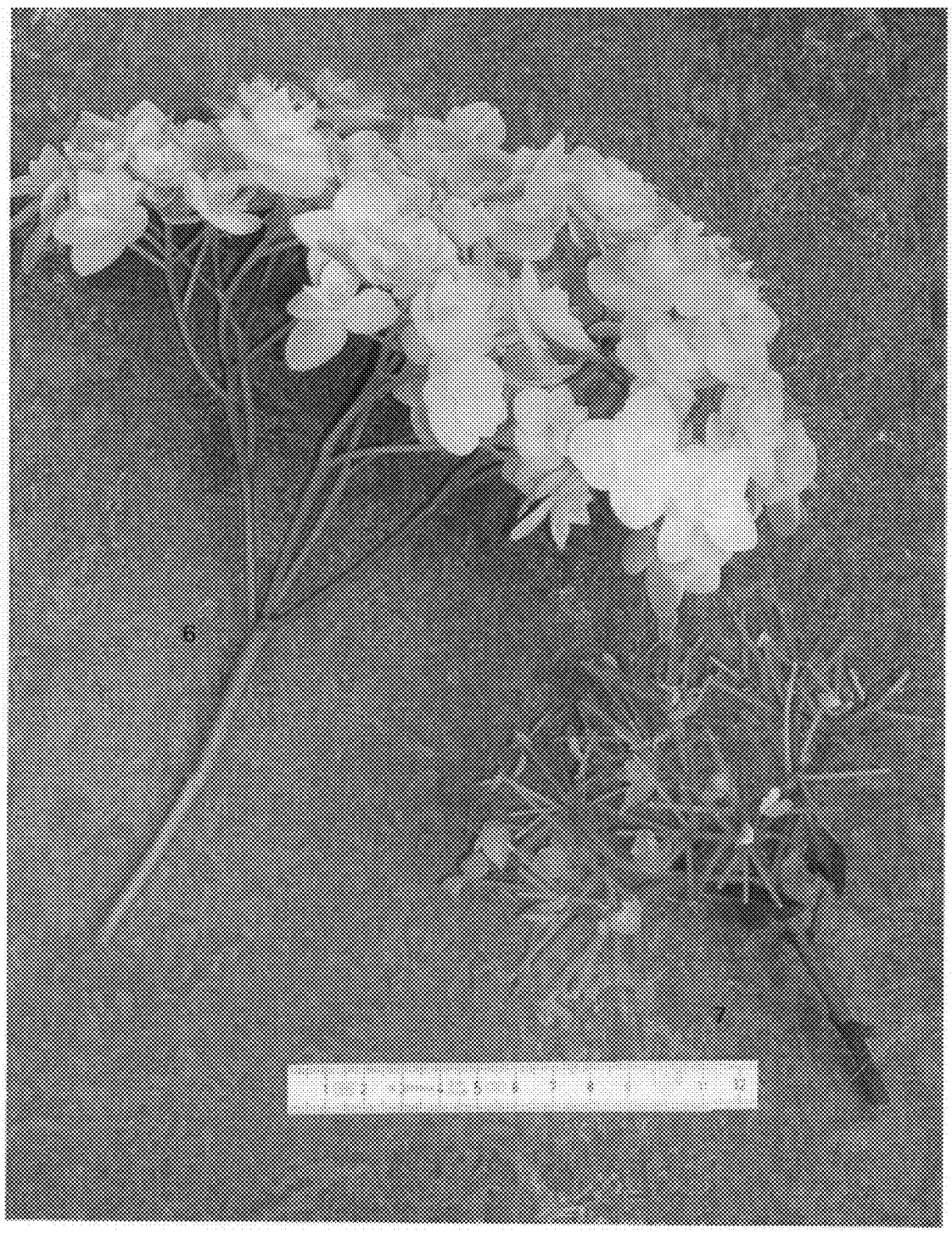

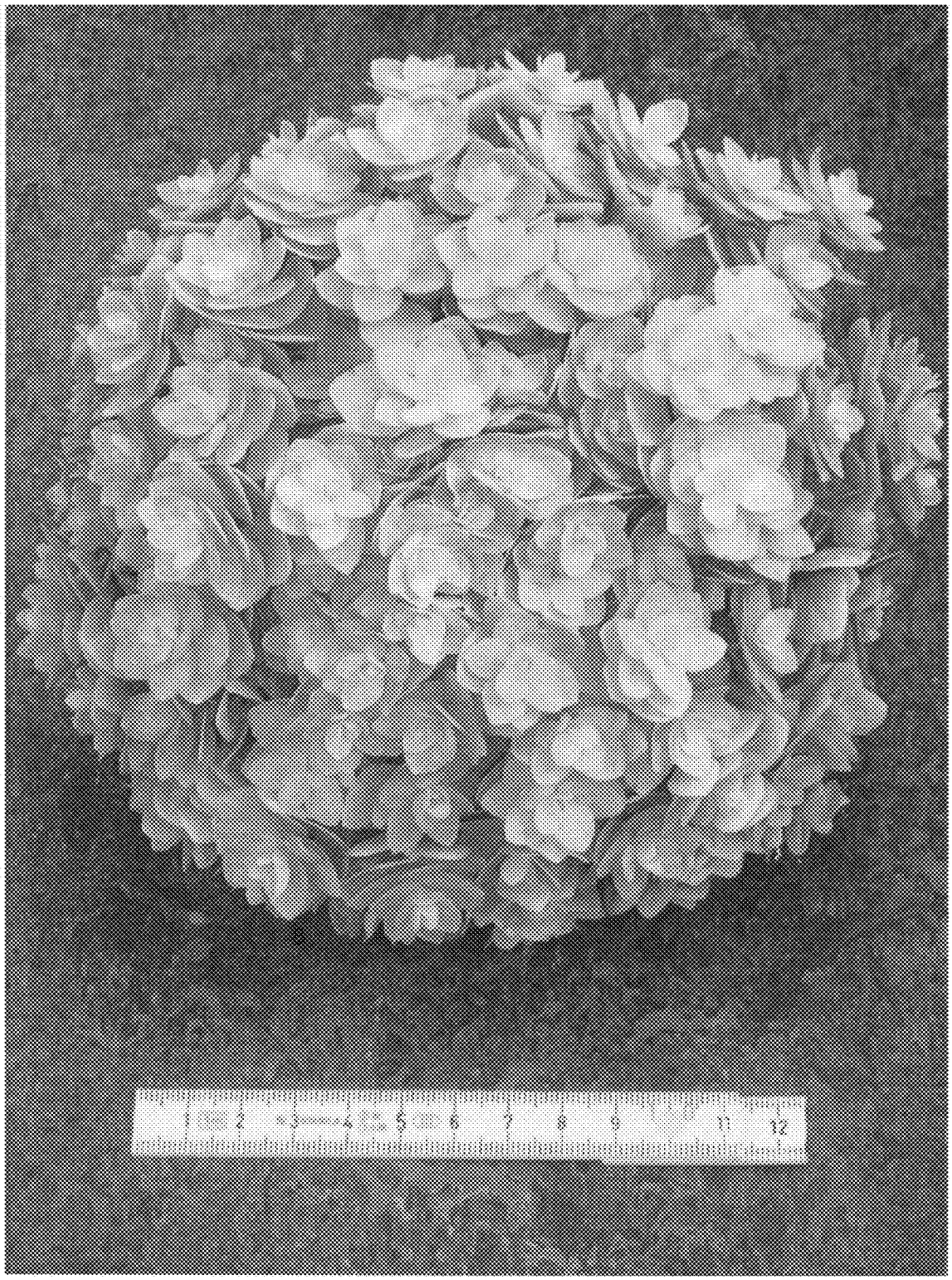

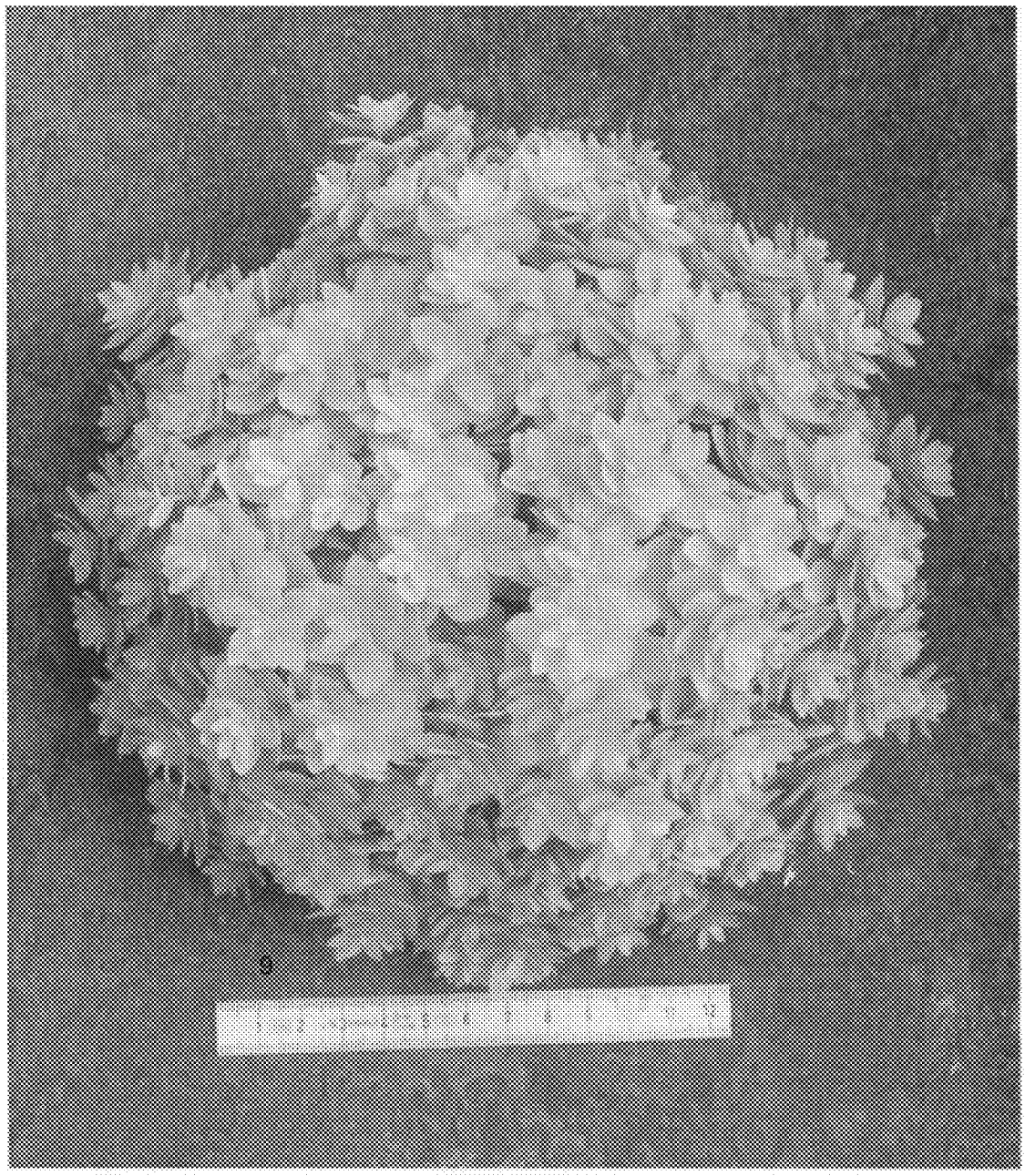

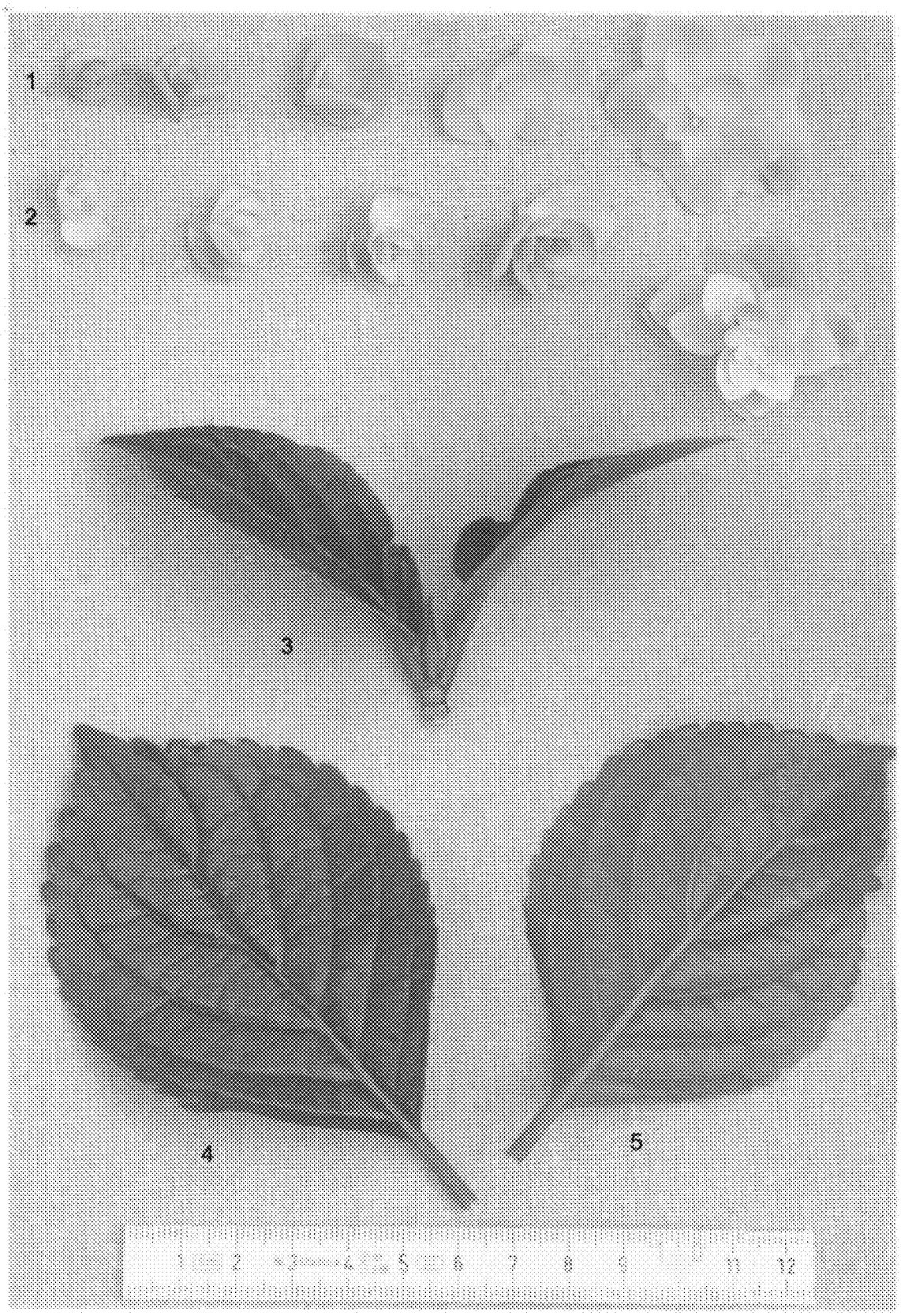
1
2
3
4
5